United States Patent [19]

Kado

[11] Patent Number: 4,520,106
[45] Date of Patent: May 28, 1985

[54] TARTRATE CATABOLISM GENE

[75] Inventor: Clarence I. Kado, Davis, Calif.

[73] Assignee: The Regents of the University of California, Berkeley, Calif.

[21] Appl. No.: 405,976

[22] Filed: Aug. 9, 1982

Related U.S. Application Data

[63] Continuation-in-part of Ser. No. 221,114, Dec. 29, 1980, abandoned.

[51] Int. Cl.³ .................. C12N 15/00; C12N 1/20; C12N 1/00
[52] U.S. Cl. .................. 435/172.3; 435/253; 435/243; 435/317; 935/30; 935/60
[58] Field of Search .............. 435/172, 253, 317, 243, 435/254, 255, 256, 257, 172.3; 536/27; 935/28, 29, 30, 60

[56] References Cited

PUBLICATIONS

Kado et al., J. Bacteriology, vol. 145, No. 3, pp. 1365–1373 (Mar. 1981).
Langley et al., Mutation Res. 14, pp. 277–286 (1972).
Kerr et al., Phytopath. Z., 90 No. 2, vol. 71, pp. 172–179 (1977).
Perry et al., Phytopathology, vol. 71, No. 2, p. 249 (1981).
Figurski et al., Gene, 1 pp. 107–119 (1976).
Datta et al., Cold Springs Harbor Symposium on Quantitive Biology 55, pp. 45–51 (1980).

Primary Examiner—Alvin E. Tanenholtz
Attorney, Agent, or Firm—Townsend & Townsend

[57] ABSTRACT

DNA sequences which are capable of expressing a polypeptide with the ability to catabolize L-tartrate are incorporated into suitable vectors and used to transform both prokaryotic and eukaryotic hosts.

3 Claims, 1 Drawing Figure

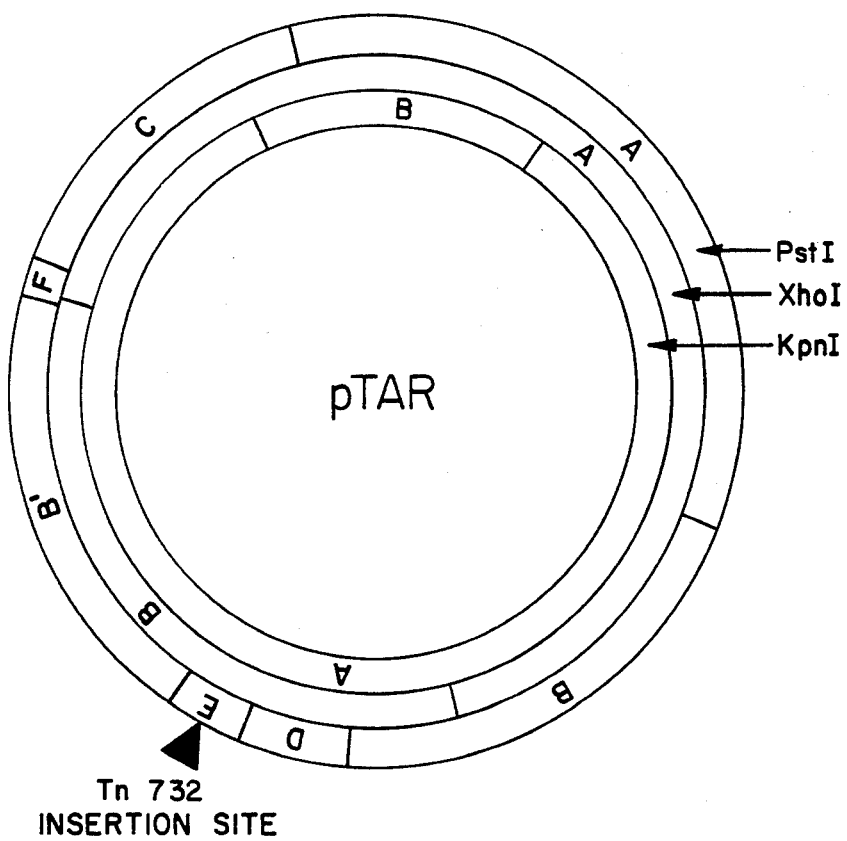
FIG._1.

… (1)

TARTRATE CATABOLISM GENE

This invention was made with government support under Grant No. CA-11526 awarded by the Department of Health and Human Services. The government has certain rights to this invention.

The following application is a continuation-in-part of application Ser. No. 221,114, filed Dec. 29, 1980, now abandoned entitled Mini-Plasmids as Gene Vectors for Plants, in the name of Clarence Kado.

BACKGROUND OF THE INVENTION

The ability to catabolize tartrate and utilize tartrate as a carbon source is very rare in microorganisms. It would be desirable to identify and isolate a gene which is able to confer the ability to utilize tartrate on a suitable host. For example, yeast used to ferment juice to alcohol are unable to utilize tartrate which is a by-product of fermentation. Introduction of a functional tartrate gene into yeast would allow the organism to utilize this additional energy source, leading to the production of additional alcohol from a given amount of juice. The trait would also be useful when it is desired to produce wine free of tartrate.

SUMMARY OF THE INVENTION

DNA sequences expressing polypeptides having the ability to catabolize L-tartrate are provided. Vectors incorporating the DNA sequences are used to transform a susceptible host to utilize L-tartrate as a carbon source.

BRIEF DESCRIPTION OF THE DRAWING

FIG. 1 illustrates the restriction pattern of pTAR giving letter designations for the fragments and indicating the relative sizes.

DESCRIPTION OF THE SPECIFIC EMBODIMENTS

The DNA sequences of the present invention appear to be less than about 20 kbp, probably less than about 10 kbp, and can be derived directly or indirectly from the TAR gene found in the pTAR plasmid of certain strains of *Agrobacterium tumefaciens*, as well as from the genome of a certain large cryptic plasmid (exceeding 200 megadaltons) found in certain biotype 3 strains of *A. tumefaciens*, including the strains designated 9-3, 14-1, 23-4, 24-2, 37G4, 52BA1, 56A2, 58-1, 70D4, 7384, and 77B2. Perry and Kado, Phytopath. (1981) 71:249.

The TAR gene may be obtained from the appropriate strain of *A. tumefaciens* by conventional techniques. For example, messenger RNA (mRNA) can be isolated and complementary DNA (cDNA) synthesized using reverse transcriptase. Alternatively, endonucleases may be used to cleave available restriction sites on either side of the TAR gene in the pTAR plasmid, or other TAR-bearing plasmid.

The pTAR plasmid may be isolated and purified from particular strains by conventional techniques. Conveniently, *A. tumefaciens* 1D1422 is lysed and the RNA hydrolyzed. This strain has been deposited at the A.T.C.C. for patent purposes on Dec. 23, 1980, and given designation 31779. The chromosomal DNA is fragmented, typically by mechanical shearing, and the resulting lysate extracted with organic solvents, conveniently phenol followed by chloroform having from about 2 to 5 volume percent isoamyl alcohol. The remaining aqueous solution of DNA is then gradient density centrifuged and the plasmid DNA isolated and subjected to conventional purification. Methods for isolating pure plasmid DNA from cleared lysates are described in Old and Primrose, *Principles of Gene Manipulation*, U. California Press, 1981, pp. 29–31.

The DNA sequences of the present invention will often include regions other than the structural gene encoding the polypeptides responsible for the tartrate utilization. Depending on the contemplated host, various regulatory and other regions can be included in the sequence, typically including an origin of replication, a promoter region and markers for the selection of transformants. In general, such DNA sequences will provide regulatory signals for expression, amplification, and for a regulated response to a variety of conditions and reagents.

It will often be desirable to provide for replication and regulation capability in both eukaryotic and prokaryotic hosts, which allows amplification of the vector in a prokryotic host while retaining the ability to be expressed in eukaryotic hosts. Such vectors are referred to as shuttle vectors.

Various markers may be employed for selection of transformants, including biocide resistance, particularly to antibiotics, such as ampicillin, tetracycline, trimethoprim, chloramphenicol, and penicillin; toxins, such as colicin; and heavy metals, such as mercuric salts. Alternatively, complementation providing an essential nutrient to an auxotrophic host may be employed. The ability to utilize tartrate as the sole carbon source can also provide a selective marker. Often, different screening markers will be required for both the prokaryotic and the eukaryotic hosts, although in some cases both types of organisms may be able to express the same markers.

Hosts which may be employed for the production of the polypeptides of the present invention include unicellular microorganisms, such as prokaryotes, i.e. bacteria; and eukaryotes, such as fungi, including yeasts, algae, protozoa, molds and the like. Specific bacteria which are susceptible to transformation include members of the Enterobacteriaceae, such as strains of *Escherichia coli;* Salmonella; Bacillaceae, such as *Bacillus subtilis;* Pneumococcus; Streptococcus; and *Haemophilus influenzae*. Specific yeasts which are of interest include *Saccharomyces cerevisiae* and *Saccharomyces sacchrin.*

The DNA sequences can be introduced directly into the genome of the host or can be first incorporated into a vector which is then introduced into the host. Exemplary methods of direct incorporation include transduction by bacteriophages, transfection where specially treated host bacterial cells can be caused to take up naked phage chromosomes, and transformation by calcium precipitation. These methods are well known and need not be described further. Exemplary vectors include plasmids, cosmids and viruses. The availability and use of such vectors are described in Old and Primrose, supra., Chapters 3–5, which are incorporated herein by reference.

When incorporated into a host according to the above-described techniques, the DNA sequences of the present invention are able to confer the ability to catabolize the L isomer of tartrate. This phenotypic trait is useful under a variety of circumstances. For example, transformed microorganisms or hosts can be used to resolve a racemic mixture of tartrate by removing substantially all the L isomer from the mixture. Alternatively, the polypeptides responsible for L-tartrate degradation can be obtained from suitably modified microorganisms, purified and used to achieve such resolution.

The trait is particularly useful in that it allows a microorganism to utilize tartrate as a carbon source when previously it was incapable of such utilization. For example, tartaric acid is a byproduct in the fermentation of juice for the production of alcohol. Introduction of a functional tartrate gene into yeast responsible for fermentation would allow the organisms to convert the tartaric acid into additional alcohol.

EXPERIMENTAL

*All temperatures are °C. and all percentages are by weight, unless otherwise indicated.

1. Isolation of Plasmid DNA from *Agrobacterium tumefaciens*.

Cells are grown in 1 liter of Luria broth for 15-20 hours at 23° C. with aeration. The cells are then harvested by centrifugation (10,000×g, 10 min), washed once with TES buffer (50 mM Tris-Cl, pH 8.0, 5 mM Na$_2$EDTA, 50 mM NaCl) and the cell pellet frozen at −20° C. The cell pellet is thawed and resuspended in 28 ml of TNS buffer (10 mM Tris-Cl, pH 8.0, 100 mM NaCl, 20% sucrose) and 9 ml of freshly prepared egg white lysozyme (10 mg/ml in 120 mM Tris-Cl, pH 8.0, 50 mM Na$_2$EDTA) is added. After 30 min incubation on ice, 3.8 ml of pancreatic ribonuclease (1 mg/ml, heat-treated at 85°, 10 min to remove any deoxyribonuclease) is added. After 15 min at room temperature, 12 ml of 0.5 M Na$_2$EDTA, pH 8.0 and 27 ml of lysis solution (100 mM Tris-Cl, pH 8.0, 50 mM Na$_2$EDTA, 500 mM CaCl, 2% sarkosyl NL97) is added. The solution is incubated in ice for 20 min and the chromosomal DNA is sheared by passing the DNA solution through a no. 18 gauge needle using a 50 ml syringe twenty times. The lysate is extracted twice with phenol (distilled and equilibrated with TES before use). The mixture is emulsified by shaking and then centrifuged at 5000×g, 20 min. The aqueous phase is collected and extracted twice with an equal volume of chloroform-isoamyl alcohol (24:1, vol/vol). Each time the organic solvent phase is removed by filtration through Whatman 1 PS paper. CsCl and ethidium bromide are added to the aqueous phase to a final density of 1.395 g/cm and 380 μg ethidium bromide per ml of DNA solution. The mixture is placed in polyallomer centrifuge tubes prerinsed with ethanol and dried, and is centrifuged for 72 hours at 35,000 rpm, 20° C. in a Spinco type 60 Ti rotor in a Beckman L350 ultracentrifuge. The plasmid DNA is withdrawn from the side of the centrifuge tube using a 3 ml syringe equipped with a no. 18 gauge hypodermic needle. The plasmid band visualized with ultraviolet light can be easily seen below the broad band composed of chromosomal and linear DNA. The plasmid DNA is subjected to a second round of centrifugation and purification in a Type 65 rotor. Ethidium bromide is removed from the final plasmid DNA solution by several extractions with water saturated n-butanol followed by dialysis against six changes of 3 liters of 10 mM Tris-Cl, pH 8.0, 1 mM Na$_2$EDTA, 4° C.

2. pTAR Plasmid is Responsible for Catabolism of L-Tartrate

*A. tumefaciens* SS18 and ID1119 were isolated from galls removed from field grapevines (*Vitis vinifera*). Strain SS18 is avirulent, harboring only the pTAR plasmid and is unable to grow on octopine or nopaline; ID1119, on the other hand, is a virulent strain that contains, in addition to an octopine type Ti plasmid, a smaller plasmid that shares DNA sequence homology with pTAR (see below). Both strains align with biotype I strains in that they will convert lactose to 3-ketolactose and utilize melezitose. Kerr and Panagopoulos, Phytopath. Zeitschr. (1977), 90:172–79. However, unlike most biotype I strains, ID1119 and SS18 will utilize L-tartaric acid as the sole carbon source in a basal salts medium. Other well characterized biotype I strains, e.g., 1D1, B$_6$(806), C58, ACH-5 and 1D135, are unable to grow on tartrate. As shown by agarose gel electrophoresis of the plasmid DNA, from strains SS18, 1D119, B$_6$(806), ACH-5, 1D1 (ATCC No. 19599), C58 and 1D135, strain SS18 harbors only the 44 kb pTAR plasmid. It appears, therefore, that tartrate utilization is not correlated with any Ti plasmid coded functions such as octopine or nopaline utilization.

Transfer of pTAR by mating SS18 (pTAR) with a plasmid-free *A. tumefaciens* recipient NT1RE could not be accomplished, even in the presence of L-tartrate, suggesting that pTAR might be transfer deficient. However, pTAR was successfully transferred into NT1RE by cotransformation with a mixture of purified pTAR DNA and pTiACH5 DNA.

Because it was found that tartrate and octopine utilization are independent functions, octopine strain ACH5 was transformed with nopaline strain L58. Transformants obtained at a frequency of $5 \times 10^{-7}$ were selected on the basis of growth on basal salts medium (Langey and Kado, Mutation Res. (1972), 14:277–286) containing 0.1% octopine 100 μg/ml rifampicin and 150μg/ml erythromycin. Each transformant was screened for growth on L-tartrate agar, and electrophoresis on agarose gel indicated that all L-tartrate utilizers harbored the large pTiACH5 plasmid and the smaller pTAR plasmid. They no longer harbored a large 280 mdal cryptic plasmid that is observed in the wild-type strain ACH5.

Transformants unable to grown on L-tartrate contained this large cryptic plasmid and the pTiACH5 plasmid. These results suggested that pTAR carries the genetic information for L-tartrate utilization. Also, pTAR may be incompatible with the large cryptic plasmid. This observation is supported by the fact that transformable strains B$_6$806, C58 and NT1, which harbor very large cryptic plasmids (megacryptic plasmids), were refactory to transformation with pTAR DNA despite repeated attempts. It was found, however, that Ti plasmids from these strains are able to coexist with pTAR when inserted by transformation into SS18.

To further establish that pTAR carries genetic information for L-tartaric acid utilization, the transposon Tn732, which confers gentamicin resistance, was inserted into pTAR. Insertion mutants were obtained by transferring Tn732, into strain SS18 by conjugation with *Escherichia coli* HB101 (RK2:Mu$_{cts}$::Tn732). The RK2::Mu$_{cts}$ vector plasmid DF210 (Figurski et al., Gene (1976), 1:107–119) undergoes abortive replication at 37° C., ensuring that it does not persist in the recipient cells. Tn732 is a large transposon measuring 10.9 kb (Datta et al., Cold Springs Harbor Symps. Quant. Biol. (1981), 65:45–51) and its size is sufficient to displace pTAR plasmid DNA from its normal position in agarose gels after electrophoresis. Thus, pTAR plasmid with Tn732 insertions were easily detected by examining individual colonies by a rapid mini-screening procedure (Kado and Liu, J. Bacteriol. (1981), 145:1365–73). Gentamicin resistant colonies of SS18(pTAR) obtained at a frequency of $10^{-6}$ of the donor Agrobacterium cells were screened for their inability to catabolize L-tartrate by replicating the colonies en masse onto minimal salts agar containing 0.3% tartrate and 100 μg/ml gentamicin sulfate at 37° C. Examination of more than 5000 colonies produced none that failed to grow on tartaric acid as the sole carbon and energy source. Subsequently, 200 of these colonies were lysed and the plasmids examined electrophoretically.

The surprising result of this study was that up to 50% of the transposants contained pTAR in addition to a pTAR::Tn732 cointegrate molecule. These two plasmid species appear to exist in harmony and are inseparable at the single colony level. However, four colonies were detected that harbored only a 55 kb plasmid. Purification of these plasmids revealed that they were indeed the result of an insertional event involving Tn732, and that three of the four were identical at the level of resolution obtained by EcoRI digestion. Reference to the physical map of the wild-type pTAR plasmid (FIG. 1) shows that these mutants had Tn732 inserted into or adjacent to PstI fragment E and that it is also present in XhoI fragment B and KpnI fragment A. Transfer of these pTAR::Tn732 plasmids into a plasmid-free strain by transformation produced transformants at a frequency of $10^{-7}$ that displayed the TAR$^-$ phenotype.

L-Tartrate proved to be useful as a selective marker in transformation experiments with wild-type pTAR DNA and the plasmid-free recipient *A. tumefaciens* strain 12D12. The co-existence of pTAR and pTi indicates a compatible relationship in Agrobacterium. DNA sequence homologies between pTAR DNA and octopine and nopaline Ti plasmids were not detected by reciprocal blot hybridization and analysis (Southern). This further substantiates the distinction between the two plasmids and also supports their compatible existence in Agrobacterium.

The procedure for the analysis was as follows: SmaI restricted pTi DNA of strains 15955, C58 and SS18 were each probed with pTi15955 DNA labelled by nick translation (Rigby et al., J. Mol. Biol. (1977), 113:237-51) with [$^{32}$P]-triphosphate deoxyribonucleosides: dCTP and dATP. SmaI restricted pTi DNA of strains C58, 19599 and pTAR were probed with labelled pTiC58 DNA. In both hybridizations, pTAR DNA was digested with PstI ad SalI. PstI restricted pTi DNA of strains SS18, C58 and 15955 were probed with labelled pTAR DNA. Blot hybridizations were performed according to Wahl et al., PNAS USA (1979), 76:3683-87 at 42° C.

Plasmid DNA blot hybridization analysis of virulent wild-type tartrate utilizing strain 1D1119 revealed DNA sequence homologies between pTAR DNA and the DNA of a plasmid of identical size in 1D1119. Quantitative estimates indicated that 20% of the pTAR DNA sequences were present. Thus, pTAR-like plasmids and the pTi plasmid seem to coexist in nature.

Analysis of large numbers of freshly isolated *A. tumefaciens* may prove this to be the case in certain ecological niches beneficial to *A. tumefaciens*. One such niche may be defined by the host in which the particular *A. tumefaciens* strain invades and multiplies during infection to produce crown gall tumors. Strain SS18 and 1D1119 were isolated from grapevine galls originating from Hungary and California respectively. A survey of *A. tumefaciens* strains freshly isolated from grapevine galls in California showed that they all utilized L-tartrate. On the other hand, strains originally isolated from other types of host plants such as plum, cherry, peach, and tomato which were the original hosts of strains ACH5, C58, 1D135 and B6(806), were unable to utilize L-tartrate.

It was also shown that biotype 3 strains of *A. tumefaciens*, usually associated with grapevines, do not carry a plasmid similar in size to pTAR but they all harbor large cryptic plasmids >200 megadalton. Nevertheless, they all utilize L-tartaric acid as the sole source of carbon. This suggests that TAR genes, of either megacryptic plasmid of chromosomal origin, may also be operating in pTAR-free strains. Because pTAR seems incompatible with the megacryptic plasmid, the possibility exists that they may have certain genetic homologies.

Although the foregoing invention has been described in some detail by way of illustration and example for purposes of clarity of understanding, it will be obvious that certain changes and modifications may be practiced within the scope of the appended claims.

What is claimed is:

1. A method for making an incompetent unicellular microorganism host competent to utilize L-tartrate as a carbon source, said method comprising introducing in vitro a plasmid conferring the ability to utilize L-tartrate into the host, said plasmid being capable of expressing a tartrate catabolism gene derived from plasmid pTAR.

2. An incompetent unicellular microorganism host made competent to utilize L-tartrate by the method of claim 1.

3. A prokaryotic host as in claim 2.

* * * * *